United States Patent [19]

Giampapa

[11] Patent Number: 5,895,652
[45] Date of Patent: Apr. 20, 1999

[54] METHOD OF METABOLIC ADJUVANATION AND CELLULAR REPAIR

[75] Inventor: Vincent C. Giampapa, Montclair, N.J.

[73] Assignee: Longevity Institute International, Montclair, N.J.

[21] Appl. No.: 08/898,090

[22] Filed: Jul. 23, 1997

Related U.S. Application Data

[63] Continuation-in-part of application No. 08/688,267, Jul. 29, 1996, abandoned.
[51] Int. Cl.$^6$ .......................... A61K 35/78; A61K 38/43; A23L 1/30; A23L 1/222
[52] U.S. Cl. .................... 424/195.1; 424/94.1; 424/439; 424/520; 424/523; 424/554; 424/556; 424/562; 424/563; 424/617; 426/72; 426/615; 426/648; 426/655; 426/651; 426/656
[58] Field of Search ................................... 424/94.1, 520, 424/195.1, 439, 523, 554, 556, 562, 563, 617; 426/615, 648, 655, 72, 651, 656

[56] References Cited

PUBLICATIONS

Krause and Mahan. Food, Nutrition, and Diet Therapy, 7th ed. (e.g., pp. 9–23 and 974–977), 1984.

*Primary Examiner*—Leon B. Lankford, Jr.
*Assistant Examiner*—Christopher R. Tate
*Attorney, Agent, or Firm*—M. K. Silverman

[57] ABSTRACT

A multi-agent tri-daily comestible of vitamin, mineral, plant extracts, aminos, neurochemical precursors, enzymes, and Ph regulating agents which supply key elements necessary for proper metabolization and function of the human body delivered at specific times of the daily biocycle when the need for such specific agents exists in order to maximize the body's extra- and intra-cellular matrix to cellular and biochemical protective and repair mechanisms utilized to deter the effects of otherwise normal aging.

3 Claims, No Drawings

METHOD OF METABOLIC ADJUVANATION AND CELLULAR REPAIR

REFERENCE TO RELATED APPLICATION

This application is a continuation-in-part of application Ser. No. 08/688,267, filed Jul. 29, 1996, entitled Method of Metabolic Adjuvanation, now abandoned.

BACKGROUND OF THE INVENTION

The principal purpose of the instant invention is that of a provision of a program of oral supplementation to augment what is termed the cellular soup. The cellular soup constitutes extra-cellular and intra-cellular fluid which acts to nourish the extra-cellular matrix, such as tissue and nerves, and the intra-cellular matrix which comprises the inner structure of the cells, this including the cell nucleus and the mitrocondria which are the energy producing elements within every living cell. The cell nucleus is where most genetic functions occur including the aging process. Accordingly, proper nourishment to the cell nucleus and mitrocondria is an essential aspect of any anti-aging therapy.

Within the cellular soups are many organic compounds which affect the metabolic process. These including vitamins, minerals, enzymes, amino acids, pre-hormones (known as hormonal precursors), co-factors, and anti-oxidants. Each of these agents affect the cellular soup and thereby human metabolism in a particular and distinct fashion. Also, all are necessary to maintain proper metabolic function and to revitalize the basic constituents of the cellular soup to effect cell repair, notably, the cell nucleus and mitochondria to halt, and to a substantial extent, reverse the aging process.

It is accordingly essential to maintain, within the cellular soup, high levels of antioxidants, hormonal precursors, RNA, DNA and other agents which otherwise decrease with age. Accordingly, by vitalizing, and continually revitalizing, the cellular soup, essential components of cells of the human body will not sense "environmental changes" which they have been genetically taught to associate with the aging process. Therefore, to the extent that contemporary knowledge of genetics has been able to relate the aging process to the status of metabolic functions, the basic building blocks of cell, namely, its nucleus and mitochondria, can be deceived into believing that no age-related metabolic changes have occurred and, therefore, that there is no reason to change their normal reproductive function of cell replacement.

In other words, the aging process is believed to relate to the failure of cell components such as the cell nucleus to continue to replicate otherwise healthy cells. This is believed to occur as a result of damage which occurs to essential cell components resultant of drops in levels of key chemical agents, including specifically those set forth above. These agents will typically diminish as a result of reduction in efficiency over time of glands and organs in the human body. Reductions in such key chemical agents are believed to cause damage to the RNA and DNA in each cell nucleus which thereby reduces the ability of the cell to reproduce itself which ultimately brings on the aging process which yet further accelerates a drop in body's production of the key agents set forth above. Accordingly, the essential problem in stopping the aging process is that of maintaining appropriate levels of key metabolic agents so that the genetic material within each cell will not become damaged or otherwise lose efficiency. Stated otherwise, it is believed that the genetic material of each cell has no way of knowing how old it is, except with reference to the intra-cellular fluid in which it is immersed. So that, if the extra-cellular fluid is kept youthful, the genetic material within each cell will continue to function in a normal fashion, without decrease in efficiency thereof.

Also of importance in halting the aging process is maintaining the health of the cell surface membrane which is the surface which delineates the extra-from the intra cellular fluid. This cell surface membrane mediates flow of essential metabolic agents between the extra-and intra cellular fluid through the function of receptor sites upon the surface membrane of each cell. There exist numerous types of receptor sites which regulate a wide variety of amino acids, hormonal and anti-oxidant transfer between the extra and intra cellular fluids. Also, the cell surface membrane plays an essential role in the function of so-called ionic pathways between the extra and intra cellular fluid, these facilitating the movement of certain agents, such as minerals, which move electro statically between the extra and intra cellular fluid.

The present invention may, accordingly, be viewed in terms of an oral supplementation program designed to restore the integrity of the cellular soup, to neutralize efficiency-impeding end products of metabolism which relate to the aging process, and to supply higher, more useful levels of anti-oxidants to better combat otherwise damaging free radicals. With such reduction of free radicals, essential hormonal pre-precursors, including neural hormonal precursors which are essential to the health of brain related glands and the central nervous system, and the building blocks of DNA are preserved. The instant oral therapy program is therefore designed to supplement all cell matrices to thereby ensure provision of necessary hormonal precursors, enzymes, and other necessary building blocks of each cell.

Another key component of the present oral therapy is known as pH balancing factors. It has been found that normal cellular pH, i.e., should be in the range of 6.45 to 7.5. It has been found that if the extra or intra cellular fluid is either too acid (above said range) or too basic (below the range), the entire metabolic process will function suboptimally. Accordingly, the present oral supplementation, through its provision of blue/green algaes ensures the maintenance of a proper pH range in the cellular soup. It has, more particularly, been determined that in the absence of proper pH, the ability of the cell to properly reproduce polypeptide and proteins is impacted as is the functions of the cell regeneration and of signal transduction, i.e., production of the chemical messengers which enable cells and tissues to communicate with each other.

This invention more particularly relates to a multi-agent tri-daily comestible which allows the supply of the equivalent of numerous vitamins, minerals, amino acids, enzymes, supplements, neuro-hormonal precursors, with phytoextracts from plants and precursors for augmenting DNA repair and limiting DNA damage. This invention provides the key vitamins, amino acids, minerals, and several components of plants and algae which are not obtainable through the average daily diet.

The comestible is then taken three times daily in order to maximize the utilization of the vitamins, minerals, amino acids, neurochemical precursors and other nutrients through matching the intake of the comestible with the needs of the body's natural bio-rhythm. Studies have shown that the administration of such vitamin and mineral supplements three times daily result in a much improved level of vitamin and mineral utilization, especially at the cellular level of metabolization. The aid in digestion of food helps the body as the body's own metabolization process decreases with age.

It has also been indicated in studies that key substances can be included that are particular to male or female requirements. Such substances include saw palmetto extract in the male supplement, which helps to alleviate prostrate enlargement, and melatonin as an important immunomodulator which helps to prevent breast cancer in women. Accordingly, the present invention uses these two substances for the corresponding sexes in the evening doses.

It is thereby to be understood that the present oral supplementation program is designed to provide, at times corresponding to the body's natural bio-rhythm, essential pH balancing agents, hormonal precursors and DNA/RNA protecting agents. The maintenance of a proper level of hormones and hormone precursors is essential to maintain the ability of the body to produce such essential agents as insulin growth factor (IGF), the function of which is to provide growth hormones which, among other functions, stabilize the body against insulin reaction. The growth hormone is further responsible for enabling amino acids and polypeptides with the cell to reach the cell nucleus to thereby enable the cell to properly divide and regenerate itself. IGF also enables polypetides and amino acids to mediate the cellular membrane for the proper nourishment of the cell and helps other agents reach the intracellular fluid. Accordingly, hormone precursors are essential to optimize the body's hormonal response to aging. More particularly, the most significant hormones which relate to aging are believed to be released by the pituitary and thymus glands. As such, through the present oral supplementation program, key hormonal components are strategically enabled, thereby regulating age related hormones and hormone precursors.

A further benefit of the instant oral supplemental program is that of augmenting the key enzymes which aid in human digestion. That is, protecting and assisting the function of the stomach and intestinal system. It has been found that an individual that ingests all necessary metabolic agents will not necessarily achieve the above set forth anti-aging benefits if the digestive tract is unable to efficiently process such agents. Accordingly, an essential aspect of the present system is that of enhancing those enzymes which are essential to human digestion to assure that an individual employing the present system will be able to digest the same in an efficient way so that the anticipated benefits of the system can be realized.

In addition, it has been found that, with age, the efficiency of the intestine or gut will deteriorate. Accordingly, the ability to utilize nutrients in an efficient manner drops as a function of age, thereby accelerating the aging process. Thus, the present inventor has discovered that no program of nutrient and anti-free radical supplementation can be successful unless those enzymes which aid digestion and which otherwise protect the intestinal tract are a part of such a system.

The prior art, as is known to the inventor, consists of individual and multiple vitamin and supplements which only give partial benefits relative to those of the instant invention. None of the vitamin or mineral supplements, or other prior art known to the inventor, address the problem addressed by the instant invention. That is, no other vitamin or mineral supplement system provides needed supplements in a manner synchronous with the bio-rhythmic demands which dictate the timing of biologic need for specific doses of supplements which are required for specific times in the cell repair cycle.

The prior art in the present area is represented by such publications as Food, Nutrition, and Diet Therapy—a Textbook of Nutritional Care, by Krause and Mahan published by W. B. Saunders Co., 1984. This paper and others of its type properly recognize the effect of aging upon metabolic functions but fail to recognize that it is metabolic changes which affect the aging process, not vice versa. Further, the prior art as represented in the above does not recognize the effect of the daily bio-cycle upon the capacity of vital organs, such as the pituitary, thalamus and pancreas, in producing hormones as a function of the time of the day when hormone related agents are ingested. Further, the prior art does not adequately recognize the significance of the pH of cellular fluids in maintaining metabolic efficiency. Also, the prior art does not correlate efficiency of the digestive tract to capacity of an individual to efficiently metabolize essential nutrients including vitamins, minerals, amino acids, and neuro hormonal precursors in order to form the essential hormones of the endocrine system. Accordingly, prior art therapies do no include digestive tract enzymes in any anti-aging regimen.

SUMMARY OF THE INVENTION

The instant method of metabolic adjuvanation and cellular repair includes the steps of (a) determining the daily vitamin, mineral, amino, neurohormonal precursor, and enzymatic needs of a subject; (b) ascertaining those periods of said subject's daily biocycle at which each vitamin, mineral, amino acids, neurohormonal precursor and enzymatic compound can be optimally absorbed; and (c) furnishing to the subject, at said periods, selected combinations and quantities of such vitamins, minerals, aminos, neurohormonal precursors, and enzymes that are optimal, for each of such biocycle period, in a palatable comestible binder of suitable geometry. Therein resulting in therapeutically sustained levels of said components act to maximize the body's inherent biochemical pathways to thereby limit damage otherwise caused by deficiencies during the normal aging process.

The present invention also relates to a multi-agent tri-daily comestible of vitamin, mineral, plant extracts, amino acids, neurochemical precursors, digestive enzymes and other agents which supply key elements necessary for proper metabolization and function of the human body at times of the daily biocycle when the need for such specific agents exists.

It is an object of the invention to provide a system to biochemically supplement all necessary vitamins, minerals and other nutrients to maintain proper cell, metabolism and body function in an individual comestible taken three times daily.

It is another object to supply the body with key vitamins, minerals and other nutrients to aid the body in metabolization of food complexes, to thereby assist in cellular regeneration and immune system repair, and to augment DNA repair thereby decreasing age-related DNA damage.

It is a further object of the invention to reduce the effect of aging by increasing the digestive and metabolic capabilities of the body.

It is another object to provide a comprehensive vitamin, mineral and nutrient supplement system congruent with natural bio-rhythms to thereby maximize metabolization, proper hormonal formation, release, and utilization of the supplements of such a system.

It is a further object to provide appropriate acidity to both the extracullar and intracullar matrices.

DETAILED DESCRIPTION OF THE INVENTION

The above and yet other objects and advantages of the present invention will become apparent from the hereinafter set forth Detailed Description of the Invention.

The instant invention may be embodied as an edible comestible, reasonably sized so one may easily swallow the comestible whole, in three separate chemical combinations for administration at various times during the day. These times are morning, midday and at night prior to sleep. These separate chemical combinations can also be taken with meals.

The comestible may comprise either a gelatinous capsule or a solid media, each dissolving to release the agents upon contact with the digestive enzymes of the stomach, the small and large intestines. The individual ingredients and quantities thereof are as follows:

The Morning Comestible comprises:
 a) A vegetable complex, including:
  Beta-Carotene, 25,000 IU.
  Lycopene Extract (tomato extract), 300 mg.
  Lutien (xanthophyll), 700 mg.
  Broccoli (22:1 concentrate), 200 mg.
  Cabbage (freeze dried), 500 mg.
  Carrot Powder, 200 mg.
  Tomato powder, 200 mg.
 b) An Ascorbate-Citrus Antioxidant Complex, including:
  Vitamin C (from calcium, magnesium and niacinamide ascorbate), 1250 mg.
  Vitamin C (ascorbic acid), 1250 mg.
  Ascorbyl palmitate (fat soluble), 250 mg.
  Acerola juice powder (natural Vitamin C), 300 mg.
  Citrus Bioflavinoids, 250 mg.
  Hesperidin Complex, 250 mg.
  Bromelanin, 15 mg.
 c) A Herbal Anti-Oxidant Complex, including:
  Grape seed extract 95 % proanthcyanidin (Indena), 20 mg.
  Bilberry extract, 25% anthocyanin, 10 mg.
  Milk Thistle Extract (85.5 % silymarin), 20 mg.
 d) B Complex, including:
  Vitamin B1 (Thiamine HCL), 200 mg.
  Vitamin B2 (Riboflavin), 50 mg.
  Vitamin B3 (Niacinamide), 100 mg.
  Vitamin B3 (Niacin), 75 mg.
  Vitamin B5 (Calcium Pantothenate), 600 mg.
  Vitamin B6 (Pyridoxine HCL), 175 mg.
  Vitamin B12 (ion exchange resin), 100 mg.
  Folate triglumate, 800 mcg.
  Biotin, 200 mcg.
 e) A Vitamin-Mineral Antioxidant Complex, including:
  Vitamin E (50% synthetic) and 50% Henkel or Eastman-natural, 500 IU.
  Vitamin A, 5000 IU.
  Selenium (Selenate), 50 mcg.
  Selenium (Selenomethione), 50 mcg.
  Zinc, 20 mg.
  Zinc (Succinate), 15 mg.
 f) An Amino Acid Antioxidant Complex, including:
  Taurine, 500 mg.
  N-acetyl-cysteine (NAC), 100 mg.
  L-glutathione, 15 mg.
 g) A mineral complex, including:
  Magnesium chloride, 800 mg.
  Magnesium aspartate, 100 mg.
  Magnesium succinate, 100 mg.
  Calcium citrate, 500 mg.
  Calcium stearate, 250 mg.
  Potassium aspartate, 50 mg.
  Potassium chloride, 49 mg.
  Vitamin D3, 300 IU.
  Chromium (Niacin bound), 50 mcg.
  Chromium (picolinate), 50 mcg.
  Molybdenum (sodium molybdate), 125 mg.
  Manganese (gluconate), 5 mg.
  Iodine (kelp), 10 mcg.
 h) A Cholinergic Complex, including:
  Choline bitartrate, 500 mg.
  Phosphatidychloride, 150 mg.
  Inositol, 250 mg.
 i) Secondary Antioxidants, including:
  Dilaurylthiodipropionate, 25 mg.
  Thiodiproprionic Acid, 25 mg.
2. Silymarin, 81 mg.
3. Beta carotene, 25,000 I.U.
4. L-carnitine, 600 mg.
5. Coenzyme Q10, 30 mg.
6. DMAE/Ginkgo Bilboa, 100 mg.
7. An Essential Fatty Acid group, including:
 a) Borage oil, 400 mg.
 b) Fish Oil, 400 mg.
 c) Flax Seed Oil, 400 mg.
 d) GLA (DEPA/DHA), 100 mg.
 e) LAA, 300 mg.
 f) Omega 3(s), 120 mg.
8. Ribonucleic Acid (RNA), 500 mg.
9. Daytime Growth Hormone formula, including:
 a) L-ornithine HCl, 300 mg.
 b) L-tyrosine, 500 mg.
10. Vitamin C, 1000 mg.
11. A vegetarian enzyme group, including:
 a) Amylase, 131 mg.
 b) Protease, 131 mg.
 c) Lipase, 15 mg.
 d) Cellulase, 5 mg.
12. A chlorophyll complex, including:
 a) Copper chlorophyllin, 20 mg.
 b) Broccoli concentrate(22:1), 400 mg.
 c) Cabbage (freeze dried), 300 mg.
 d) Parsley, 100 mg.
 e) Peppermint, 50 mg.
 f) Folate triglutimate, 800 mcg.
 g) Lycopene extract (tomato), 100 mg.
 h) Beta-carotene, 5000 IU.
 i) Lutein extract, 200 mg.
13. A herbal stimulant group, including:
 a) Mahwhang Extract, 167 mg.
 b) Guta Kola Extract, 500 mg.
14. Chromium Picolinate, 100 mg.
15. Adenosine Triphosphate(ATP), 60 mg.
16. Acetyl-L-Carnithine, 250 mg.
17. A blue green Algae group, including:

a) Spirulina, 1.25 ml.
b) Aphanizaomenon Flos Aquae (AFA), 1.25 ml.
18. A glandular complex including pancreas, thymus, and adrenal extracts.

The Mid-day Comestible comprises:
1. An anti-oxidant mix, including:
   a) A vegetable complex, including:
   Beta-Carotene, 25,000 IU.
   Lycopene Extract (tomato extract), 300 mg.
   Lutien (xanthophyll), 700 mg.
   Broccoli (22:1 concentrate), 200 mg.
   Cabbage (freeze dried), 500 mg.
   Carrot Powder, 200 mg.
   Tomato powder, 200 mg.
   b) An Ascorbate-Citrus Antioxidant Complex, including:
   Vitamin C (from calcium, magnesium and niacinamide ascorbate), 1250 mg.
   Vitamin C (ascorbic acid), 1250 mg.
   Ascorbyl palmitate (fat soluble), 250 mg.
   Acerola juice powder (natural Vitamin C), 300 mg.
   Citrus Bioflavinoids, 250 mg.
   Hesperidin Complex, 250 mg.
   Bromelanin, 15 mg.
   c) A Herbal Anti-Oxidant Complex, including:
   Grape seed extract 95% proanthcyanidin (Indena), 20 mg.
   Bilberry extract, 25% anthocyanin, 10 mg.
   Milk Thistle Extract (85.5% silymarin), 20 mg.
   d) A B-Complex, including:
   Vitamin B1 (Thiamine HCL), 200 mg.
   Vitamin B2 (Riboflavin), 50 mg.
   Vitamin B3 (Niacinamide), 100 mg.
   Vitamin B3 (Niacin), 75 mg.
   Vitamin B5 (Calcium Pantothenate), 600 mg.
   Vitamin B6 (Pyridoxine HCL), 175 mg.
   Vitamin B12 (ion exchange resin), 100 mg.
   Folate triglumate, 800 mcg.
   Biotin, 200 mcg.
   e) A Vitamin-Mineral Antioxidant Complex, including:
   Vitamin E (50% synthetic) and 50% Henkel or Eastman-natural, 500 IU.
   Vitamin A, 5000 IU.
   Selenium (Selenate), 50 mcg.
   Selenium (Selenomethione), 50 mcg.
   Zinc, 20 mg.
   Zinc (Succinate), 15 mg.
   f) An Amino Acid Antioxidant Complex, including:
   Taurine, 500 mg.
   N-acetyl-cysteine (NAC), 100 mg.
   L-glutathione, 15 mg.
   g) A mineral complex, including:
   Magnesium chloride, 800 mg.
   Magnesium aspartate, 100 mg.
   Magnesium succinate, 100 mg.
   Calcium citrate, 500 mg.
   Calcium stearate, 250 mg.
   Potassium aspartate, 50 mg.
   Potassium chloride, 49 mg.
   Vitamin D3, 300 IU.
   Chromium (Niacin bound), 50 mcg.
   Chromium (picolinate), 50 mcg.
   Molybdenum (sodium molybdate), 125 mg.
   Manganese (gluconate), 5 mg.
   Iodine (kelp), 10 mcg.
   h) A cholinergic complex, including:
   Choline bitartrate, 500 mg.
   Phosphatidychloride, 150 mg.
   Inositol, 250 mg.
   i) Secondary Antioxidants, including:
   Dilaurylthiodipropionate, 25 mg.
   Thiodiproprionic Acid, 25 mg.
2. An Essential Fatty Acid group, including:
   a) Borage oil, 400 mg.
   b) Fish Oil, 400 mg.
   c) Flax Seed Oil, 400 mg.
   d) GLA (DEPA/DHA), 100 mg.
   e) LAA, 300 mg.
   f) Omega 3(s), 120 mg.
3. Ribonucleic Acid (RNA), 500 mg.
4. Proanthocyanadin, 30 mg.
5. Vitamin C, 1000 mg.
6. Ascorbyl palmitate, 500 mg.
7. A vegetarian enzyme group, including:
   a) Amylase, 131 mg.
   b) Protease, 131 mg.
   c) Lipase, 131 mg.
   d) Cellulase, 5 mg.
8. Octa-cosanol (gunach extracts)
9. Choline/inositol, 500 mg.
10. N-aceyle-carnithine, 250 mg.
11. Adenosine Triphosphate (ATP), 60 mg.
12. A Blue Green Algae group (supplying essential nucleic acids) including:
    a) Spirulina, 1.25 ml.
    b) Aphanizaomenon Flos Aquae (AFA), 1.25 ml.
13. N-acolyl glucosamine and glucasamine sulfate.

The Evening Comestible, comprises:
1. An anti-oxidant group, including:
   a) A vegetable complex, including:
   Beta-Carotene, 25,000 IU.
   Lycopene Extract (tomato extract), 300 mg.
   Lutien (xanthophyll), 700 mg.
   Broccoli (22:1 concentrate), 200 mg.
   Cabbage (freeze dried), 500 mg.
   Carrot Powder, 200 mg.
   Tomato powder, 200 mg.
   b) An Ascorbate-Citrus Antioxidant Complex, including:
   Vitamin C (from calcium, magnesium and niacinamide ascorbate), 1250 mg.
   Vitamin C (ascorbic acid), 1250 mg.
   Ascorbyl palmitate (fat soluble), 250 mg.
   Acerola juice powder (natural Vitamin C), 300 mg.
   Citrus Bioflavinoids, 250 mg.
   Hesperidin Complex, 250 mg.
   Bromelanin, 15 mg.
   c) A Herbal Anti-Oxidant Complex, including:
   Grape seed extract 95 % proanthcyanidin (Indena), 20 mg.
   Bilberry extract, 25% anthocyanin, 10 mg.
   Milk Thistle Extract (85.5% silymarin), 20 mg.
   d) A B-Complex, including:
   Vitamin B1 (Thiamine HCL), 200 mg.

Vitamin B2 (Riboflavin), 50 mg.
Vitamin B3 (Niacinamide), 100 mg.
Vitamin B3 (Niacin), 75 mg.
Vitamin B5 (Calcium Pantothenate), 600 mg.
Vitamin B6 (Pyridoxine HCL), 175 mg.
Vitamin B12 (ion exchange resin), 100 mg.
Folate triglumate, 800 mcg.
Biotin, 200 mcg.
e) A Vitamin-Mineral Antioxidant Complex, including:
Vitamin E (50% synthetic) and 50% Henkel or Eastman-natural, 500 IU.
Vitamin A, 5000 IU.
Selenium (Selenate), 50 mcg.
Selenium (Selenomethione), 50 mcg.
Zinc, 20 mg.
Zinc (Succinate), 15 mg.
f) An Amino Acid Antioxidant Complex, including:
Taurine, 500 mg.
N-acetyl-cysteine (NAC), 100 mg.
L-glutathione, 15 mg.
g) A Mineral Complex, including:
Magnesium chloride, 800 mg.
Magnesium succinate, 100 mg.
Calcium citrate, 500 mg.
Calcium stearate, 250 mg.
Potassium chloride, 49 mg.
Vitamin D3, 300 IU.
Chromium (Niacin bound), 50 mcg.
Chromium (picolinate), 50 mcg.
Molybdenum (sodium molybdate), 125 mg.
Manganese (gluconate), 5 mg.
Iodine (kelp), 10 mcg.
h) A cholinergic complex, including:
Choline bitartrate, 500 mg.
Phosphatidychloride, 150 mg.
Inositol, 250 mg.
i) Secondary Antioxidants, including:
Dilaurylthiodipropionate, 25 mg.
Thiodiproprionic Acid, 25 mg.
2. L-Carnitine, 600 mg.
3. Coenzyme Q10, 30 mg.
4. An vegetarian enzyme group, including:
a) Amylase, 131 mg.
b) Proteases, 131 mg.
c) Lipase, 15 mg.
d) Cellulase, 5 mg.
5. A chlorophyll complex, including:
a) Copper chlorophyllin, 20 mg.
b) Broccoli concentrate(22:1), 400 mg.
c) Cabbage (freeze dried), 300 mg.
d) Parsley, 100 mg.
e) Peppermint, 50 mg.
f) Folate triglutimate, 800 mcg.
g) Lycopene extract (tomato), 100 mg.
h) Beta-carotene, 5000 IU.
i) Lutein extract, 200 mg.
6. A Nighttime Growth Hormone Formula, including:
L-glutarune 2000 mg.
Niacinamida 250 mg.
7. Chromium Picolinate, 200 mg.
8. N-acetyl-carnithine, 250 mg.
9. Adenosine Triphosphate (ATP), 60 mg.
10. A blue green Algae group, including:
a) Spirulina, 1.25 ml.
b) Aphanizaomenon Flos Aquae (AFA), 1.25 ml.
11. Saw Palmetto Extract, 60 mg.;
For both male and female versions—Melatonin, 60 mg.
12. Glandular extracts—pancreas, thymus, adrenal.

The application of these specific agents at their indicated times will maximize the delivery, metabolization and use of the agents therein.

The above regimen/system is believed to (1) augment activity of the cell mitochondria to thereby enhance energy production of the cells; (2) enhance the function of the extracellular matrix as a nutrient reservoir; and (3) facilitate signal transduction of cell receptors between applicable cells; (4) augment the immune system; (5) facilitate repair of DNA and reduce metabolic damage thereof by free radicals, this slowing the aging process; (6) reset and normalize the neurohormonal monitoring system of the central nervous system, and (7) decrease the amount formed, as well as the availability of, free radicals.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

Having thus described our invention what we claim as new, useful and non-obvious and, accordingly, secure by Letters Patent of the United States is:

1. A method of providing nutritional supplements to a human subject in the form of morning, mid-day, and evening comestible having a suitable geometry in which:
(i) A morning comestible comprising:
A. an anti-oxidant mix comprising:
(a) vegetable complex, including:
beta-carotene, 25,000 IU,
lycopene extract, 300 mg.,
lutein, 700 mg.,
broccoli (preferably 22:1 concentrate), 200 mg.,
cabbage (preferably freeze dried), 500 mg.,
carrot powder, 200 mg., and
tomato powder, 200 mg.
(b) an ascorbate-citrus antioxidant complex, including:
Vitamin C (from calcium, magnesium and niacinamide ascorbate), 1250 mg.,
Vitamin C (ascorbic acid), 1250 mg.,
ascorbyl palmitate (preferably fat soluble), 250 mg.,
acerola juice powder (a natural form of Vitamin C), 300 mg.,
citrus bioflavinoids, 250 mg.,
hesperidin complex, 250 mg., and
bromelanin, 15 mg.;
(c) a herbal anti-oxidant complex, including:
grape seed extract, 95% proanthcyanidin, 20 mg.,
bilberry extract, 25% anthocyanin, 10 mg., and
milk thistle extract, 20 mg.;
(d) a B-complex, including:
Vitamin B1, 200 mg.,
Vitamin B2, 50 mg.,
Vitamin B3 (niacinamide), 100 mg.,
Vitamin B3 (niacin), 75 mg.,
Vitamin B5, 600 mg.,
Vitamin B6, 175 mg., Vitamin B12, 100 mg.,
folate triglumate, 800 mcg., and
biotin, 200 mcg.;
e) a vitamin-mineral antioxidant complex, including:
Vitamin E (preferably 50% synthetic and 50% natural), 500 IU.,
Vitamin A, 5000 IU.,
selenium (selenate form), 50 mcg.,
selenium (selenomethione form), 50 mcg.,
zinc, 20 mg., and
zinc (succinate form), 15 mg.;
f) an amino acid antioxidant complex, including:
taurine, 500 mg.,
n-acetyl-cysteine (NAC), 100 mg., and
L-glutathione, 15 mg.;
g) a mineral complex, including:
magnesium chloride, 800 mg.,
magnesium aspartate, 100 mg.,
magnesium succinate, 100 mg.,
calcium citrate, 500 mg.,
calcium stearate, 250 mg.,
potassium aspartate, 50 mg.,
potassium chloride, 49 mg.,
Vitamin D3, 300 IU.,
chromium (niacin bound form), 50 mcg.,
chromium (picolinate form), 50 mcg.
molybdenum, 125 mg.
manganese 5 mg., and
iodine, 10 mcg.;
h) a cholinergic complex, including:
choline bitartrate, 500 mg.,
phosphatidychloride, 150 mg., and
inositol, 250 mg.;
i) secondary antioxidants, including:
dilaurylthiodipropionate, 25 mg., and
thiodiproprionic acid, 25 mg.;
B. silymarin, 81 mg.;
C. beta-carotene, 25,000 I.U.;
D. L-carnitine, 600 mg.;
E. coenzyme Q10, 30 mg.;
F. dimethylaminoethenol (DMAE/ginkgo bilboa form), 100 mg.;
G. an essential fatty acid group, including:
a) borage oil, 400 mg.
b) fish oil, 400 mg.
c) flax seed oil, 400 mg.
d) docosahexaenoic (DHA), 100 mg.
e) alpha-linoic acid (ALA), 300 mg.;
f) Omega-3 oils, 120 mg.;
H. ribonucleic acid (RNA), 500 mg.;
I. a daytime growth hormone formula, including:
a) L-ornithine HCl, 300 mg., and
b) L-tyrosine, 500 mg.;
J. Vitamin C, 1000 mg.;
K. a vegetarian enzyme group, including:
a) amylase, 131 mg.,
b) protease, 131 mg.,
c) lipase, 15 mg., and
d) cellulase, 5 mg.;
L. a chlorophyll complex, including:
a) copper chlorophyllin, 20 mg.,
b) broccoli concentrate (preferably 22:1), 400 mg.,
c) cabbage (preferably freeze dried), 300 mg.,
d) parsley, 100 mg.,
e) peppermint, 50 mg.,
f) folate triglutimate, 800 mcg.,
g) lycopene extract, 100 mg.,
h) beta-carotene, 5000 IU., and
i) lutein extract, 200 mg.;
M. a herbal stimulant group, including:
a) mahwhang extract, 167 mg., and
b) guta kola Extract, 500 mg.;
N. chromium picolinate, 100 mg.;
O. adenosine triphosphate (ATP), 60 mg.;
P. acetyl-1-carnitine, 250 mg.;
Q. a blue green algae group, including:
a) Spirulina, 1.25 ml., and
b) aphanizaomenon flos aquae (AFA), 1.25 ml.;
R. a glandular complex including pancreas, thymus, and adrenal extracts;
(ii) A mid-day comestible comprising:
A. an anti-oxidant mix, including:
a) a vegetable complex, including:
beta-carotene, 25,000 IU.,
lycopene extract, 300 mg.,
lutein, 700 mg.
broccoli (preferably 22:1 concentrate), 200 mg.,
cabbage (preferably freeze dried), 500 mg.,
carrot powder, 200 mg., and
tomato powder, 200 mg.;
b) an ascorbate-citrus antioxidant complex including:
Vitamin C, (from calcium, magnesium and niacinamide ascorbate), 1250 mg.
Vitamin C (from ascorbic acid), 1250 mg.,
ascorbyl palmitate (fat soluble from), 250 mg.,
acerola juice powder (a form of natural Vitamin C), 300 mg.,
citrus bioflavinoids, 250 mg.,
hesperidin complex, 250 mg., and
bromelanin, 15 mg.;
c) a herbal anti-oxidant complex, including:
grape seed extract, 95 % proanthcyanidin, 20 mg.,
bilberry extract, 25% anthocyanin, 10 mg., and
milk thistle extract; 20 mg.;
d) a B-Complex, including:
Vitamin B1, 200 mg.,
Vitamin B2, 50 mg.,
Vitamin B3 (niacinamide), 100 mg.,
Vitamin B3 (niacin), 75 mg.,
Vitamin B5, 600 mg.,
Vitamin B6, 175 mg.,
Vitamin B12, 100 mg.,
folate triglumate, 800 mcg., and
biotin, 200 mcg.;
e) a vitamin-mineral antioxidant complex, including:
Vitamin E (50% synthetic and 50% natural), 500 IU.,
Vitamin A, 5000 IU.,
selenium (selenate form), 50 mcg.,
selenium (selenomethione), 50 mcg.,
zinc, 20 mg., and
zinc (succinate from), 15 mg.;
f) an amino acid antioxidant complex, including:
taurine, 500 mg.,
n-acetyl-cysteine (NAC), 100 mg., and
L-glutathione, 15 mg.;

g) a mineral complex, including:
   magnesium chloride, 800 mg.,
   magnesium aspartate, 100 mg.,
   magnesium succinate, 100 mg.,
   calcium citrate, 500 mg.,
   calcium stearate, 250 mg.,
   potassium aspartate, 50 mg.,
   potassium chloride, 49 mg.,
   vitamin D3, 300 IU.
   chromium (niacin bound form), 50 mcg.,
   chromium (picolinate form), 50 mcg.,
   molybdenum (sodium molybdate form), 125 mg.,
   manganese (gluconate form), 5 mg., and
   iodine, 10 mcg.;
h) a cholinergic complex, including:
   choline bitartrate, 500 mg.,
   phosphatidychloride, 150 mg., and
   inositol, 250 mg.;
i) secondary antioxidants, including:
   dilaurylthiodipropionate, 25 mg., and
   thiodiproprionic Acid, 25 mg.;
B. an essential fatty acid group, including:
a) borage oil, 400 mg.,
b) fish oil, 400 mg.,
c) flax seed oil, 400 mg.,
d) dimethylaminoethenol, 100 mg.,
e) alpha-linoic, 300 mg.;
f) omega-3 oils, 120 mg.;
C. ribonucleic acid (RNA), 500 mg.;
D. proanthocyanadin, 30 mg.;
E. Vitamin C, 1000 mg.;
F. ascorbyl palmitate, 500 mg.;
G. a vegetarian enzyme group, including:
a) amylase, 131 mg.,
b) protease, 131 mg.,
c) lipase, 131 mg., and
d) cellulase, 5 mg.;
H. octa-cosanol;
I. choline/inositol, 500 mg.;
J. n-acetyl-carnithine, 250 mg.;
K. adenosine triphosphate (ATP), 60 mg.;
L. a blue green algae group including:
a) Spirulina, 1.25 ml., and
b) aphanizaomenon flos aquae (AFA), 1.25 ml.; and
M. n-acetyl glucosamine and glucasamine sulfate; and
(iii) An evening comestible comprising:
   A. An anti-oxidant mix, including:
   a) a vegetable complex, including:
      beta-carotene, 25,000 IU.
      lycopene extract, 300 mg.
      lutein, 700 mg.,
      broccoli (preferably 22:1 concentrate), 200 mg.,
      cabbage (freeze dried), 500 mg.
      carrot powder, 200 mg., and
      tomato powder, 200 mg.;
   b) an ascorbate-citrus antioxidant complex, including:
      Vitamin C (from calcium, magnesium and niacinamide ascorbate), 1250 mg.,
      Vitamin C from (ascorbic acid), 1250 mg.,
      ascorbyl palmitate (fat soluble from), 250 mg.,
      acerola juice powder (a form of natural Vitamin C), 300 mg.

citrus bioflavinoids, 250 mg.,
hesperidin complex, 250 mg., and
bromelanin, 15 mg.;
c) an herbal anti-oxidant complex, including:
   grape seed extract, 95 % proanthcyanidin, 20 mg.
   bilberry extract, 25% anthocyanin, 10 mg., and
   milk thistle extract, 20 mg.;
d) a B-complex, including:
   Vitamin B1, 200 mg.,
   Vitamin B2, 50 mg.,
   Vitamin B3 (niacinamide), 100 mg.,
   Vitamin B3 (niacin), 75 mg.,
   Vitamin B5, 600 mg.,
   Vitamin B6, 175 mg.,
   Vitamin B12, 100 mg.,
   folate triglumate, 800 mcg.,
   biotin, 200 mcg.;
e) a vitamin-mineral antioxidant complex, including:
   Vitamin E (50% synthetic and 50% natural), 500 IU.,
   Vitamin A, 5000 IU.,
   selenium (selenate forms), 50 mcg.,
   selenium (selenomethione form), 50 mcg.,
   zinc, 20 mg., and
   zinc (succinate form), 15 mg.;
f) an amino acid antioxidant complex, including:
   taurine, 500 mg.
   n-acetyl-cysteine (NAC), 100 mg., and
   l-glutathione, 15 mg.
g) a mineral complex, including:
   magnesium chloride, 800 mg.,
   magnesium succinate, 100 mg.,
   calcium citrate, 500 mg.,
   calcium stearate, 250 mg.,
   potassium chloride, 49 mg.,
   Vitamin D3, 300 IU.,
   chromium (niacin bound form), 50 mcg.,
   chromium (picolinate), 50 mcg.
   molybdenum, 125 mg.
   manganese, 5 mg., and
   iodine, 10 mcg.;
h) a cholinergic complex, including:
   choline bitartrate, 500 mg.,
   phosphatidychloride, 150 mg., and
   inositol, 250 mg.;
i) secondary antioxidants, including:
   dilaurylthiodipropionate, 25 mg., and
   thiodiproprionic acid, 25 mg.;
B. l-carnithine, 600 mg.;
C. coenzyme Q10, 30 mg.
D. a vegetarian enzyme group, including:
a) amylase, 131 mg.,
b) proteases, 131 mg.,
c) lipase, 15 mg., and
d) cellulase, 5 mg.;
E. a chlorophyll complex, including:
a) copper chlorophyllin, 20 mg.,
b) broccoli concentrate (preferably 22:1), 400 mg.,
c) cabbage (preferably freeze dried), 300 mg.,
J. a blue green algae group, including:
a) Spirulina, 1.25 ml., and
b) aphanizaomenon flos aquae (AFA), 1.25 ml.;
K. saw palmetto extract, 60 mg.;
L. melatonin, 60 mg.; and M. a glandular complex including pancreas, thymus and adrenal extracts, thereby providing therapeutically sustained levels of said components which act enhance the body's inherent biochemical pathways to maximize the extra-and-intra-cellular matrices and, as such, limit damage including free radical change, distorted receptor sites, abnormal DNA replication, and other damage caused by nutritional deficiencies during the aging process.

2. The method as recited in claim 1 further comprising the step of:

furnishing to the subject enzymes and enzyme builders related to the health of the digestive track.

3. The method as recited in claim 2 comprising the step of:

maintaining the pH of extra and intracellular fluid matrices of the subject within a range of 6.45 to 7.45.

* * * * *